United States Patent
Perine et al.

(10) Patent No.: US 8,720,442 B2
(45) Date of Patent: *May 13, 2014

(54) SYSTEMS AND METHODS FOR MANAGING PRESSURE IN A BREATHING ASSISTANCE SYSTEM

(75) Inventors: Philippe Perine, Eulmont (FR); Julien Gentner, Chaligny (FR); Benjamin Desfossez, Nancy (FR); Pascal Nicolazzi, Gondreville (FR); Yves Gaudard, Malzeville (FR); Hossein Nadjafizadeh, Villers-les-Nancy (FR)

(73) Assignee: Covidien LP, Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/458,305

(22) Filed: Apr. 27, 2012

(65) Prior Publication Data

US 2012/0211008 A1    Aug. 23, 2012

Related U.S. Application Data

(63) Continuation of application No. 12/238,607, filed on Sep. 26, 2008, now Pat. No. 8,181,648.

(51) Int. Cl.
*A61M 16/00* (2006.01)
*A62B 7/00* (2006.01)
*A61M 16/10* (2006.01)

(52) U.S. Cl.
CPC ............ *A61M 16/10* (2013.01); *A61M 16/00* (2013.01); *A61M 2016/0027* (2013.01); *A61M 2016/0003* (2013.01)
USPC ............. 128/204.23; 128/204.18; 128/204.21

(58) Field of Classification Search
CPC ............... A61M 16/00; A61M 16/10; A61M 2016/0027; A61M 2016/0003; A61M 2205/3331
USPC ............ 128/200.24, 204.18, 204.21–204.23, 128/204.26, 205.23; 73/1.57
See application file for complete search history.

(56) References Cited

U.S. PATENT DOCUMENTS 4,752,089 A  6/1988  Carter
4,921,642 A  5/1990  LaTorraca (Continued)

FOREIGN PATENT DOCUMENTS

EP    850652    7/1998
FR    2829942 A1  3/2003  ............ A61M 16/00

(Continued)

OTHER PUBLICATIONS

"GoodKnight® 424 GoodKnight® 45ST Clinician and Home Care Provider Manual", Puritan Bennett, Revision G, p. 5, referring to breathing circuits having an "internal pressure sensor line", Mar. 2010.

(Continued)

*Primary Examiner* — Justine Yu
*Assistant Examiner* — Valerie L Skorupa
(74) *Attorney, Agent, or Firm* — Merchant & Gould P.C.

(57) ABSTRACT

A breathing assistance system for providing breathing assistance to a patient is provided. The breathing assistance system may include a ventilation system for supplying a gas flow, a conduit operatively coupled to the ventilation system, and a pressure sensor configured to measure the pressure of the gas flow through the conduit. The pressure sensor may include a structure configured to create a localized pressure drop in the gas flow proximate the pressure sensor structure.

17 Claims, 4 Drawing Sheets

(56) References Cited

U.S. PATENT DOCUMENTS

| | | |
|---|---|---|
| 4,954,799 A | 9/1990 | Kumar |
| 4,967,744 A | 11/1990 | Chua ............... 128/204.18 |
| 5,057,822 A | 10/1991 | Hoffman |
| 5,072,737 A | 12/1991 | Goulding |
| 5,099,836 A | 3/1992 | Rowland et al. ........ 128/204.23 |
| 5,111,827 A * | 5/1992 | Rantala .............. 600/532 |
| 5,146,092 A | 9/1992 | Apperson et al. |
| 5,150,291 A | 9/1992 | Cummings et al. |
| 5,153,436 A | 10/1992 | Apperson et al. |
| 5,161,525 A | 11/1992 | Kimm et al. |
| 5,237,987 A | 8/1993 | Anderson et al. |
| 5,271,389 A | 12/1993 | Isaza et al. |
| 5,279,549 A | 1/1994 | Ranford |
| 5,299,568 A | 4/1994 | Forare et al. |
| 5,301,921 A | 4/1994 | Kumar |
| 5,316,009 A | 5/1994 | Yamada |
| 5,319,540 A | 6/1994 | Isaza et al. |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | LaTorraca |
| 5,369,277 A | 11/1994 | Knodle et al. |
| 5,383,449 A | 1/1995 | Forare et al. |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,438,980 A | 8/1995 | Phillips |
| 5,443,075 A | 8/1995 | Holscher |
| 5,494,051 A | 2/1996 | Schneider, Sr. ............... 128/870 |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,542,415 A | 8/1996 | Brody |
| 5,544,674 A | 8/1996 | Kelly |
| 5,549,106 A | 8/1996 | Gruenke et al. |
| 5,596,984 A | 1/1997 | O'Mahony et al. |
| 5,616,923 A | 4/1997 | Rich et al. |
| 5,630,411 A | 5/1997 | Holscher |
| 5,632,270 A | 5/1997 | O'Mahony et al. |
| 5,645,048 A | 7/1997 | Brodsky et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,693,944 A | 12/1997 | Rich |
| 5,715,812 A | 2/1998 | Deighan et al. |
| 5,749,374 A | 5/1998 | Schneider, Sr. ............... 128/870 |
| 5,762,480 A | 6/1998 | Adahan |
| 5,771,884 A | 6/1998 | Yarnall et al. |
| 5,789,660 A | 8/1998 | Kofoed et al. |
| 5,791,339 A | 8/1998 | Winter |
| 5,794,614 A | 8/1998 | Gruenke et al. ........ 128/204.21 |
| 5,794,986 A | 8/1998 | Gansel et al. |
| 5,813,399 A | 9/1998 | Isaza et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,881,717 A | 3/1999 | Isaza |
| 5,881,723 A | 3/1999 | Wallace et al. |
| 5,884,623 A | 3/1999 | Winter |
| 5,906,204 A | 5/1999 | Beran et al. |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,934,274 A | 8/1999 | Merrick et al. |
| 5,969,429 A | 10/1999 | Rudolph et al. ............... 290/54 |
| 6,024,089 A | 2/2000 | Wallace et al. |
| 6,041,780 A | 3/2000 | Richard et al. |
| 6,047,860 A | 4/2000 | Sanders |
| 6,076,523 A | 6/2000 | Jones et al. |
| 6,095,140 A | 8/2000 | Poon et al. |
| 6,099,481 A | 8/2000 | Daniels et al. |
| 6,106,480 A | 8/2000 | Gama De Abreu et al. |
| 6,116,240 A | 9/2000 | Merrick et al. |
| 6,116,464 A | 9/2000 | Sanders |
| 6,123,073 A | 9/2000 | Schlawin et al. |
| 6,135,106 A * | 10/2000 | Dirks et al. ............... 128/204.23 |
| 6,142,150 A | 11/2000 | O'Mahoney |
| 6,155,986 A | 12/2000 | Brydon et al. |
| 6,161,539 A | 12/2000 | Winter |
| 6,179,784 B1 | 1/2001 | Daniels et al. |
| 6,203,502 B1 | 3/2001 | Hilgendorf et al. |
| 6,220,245 B1 | 4/2001 | Takabayashi et al. |
| 6,227,196 B1 | 5/2001 | Jaffe et al. |
| 6,269,812 B1 | 8/2001 | Wallace et al. |
| 6,273,444 B1 | 8/2001 | Power |
| 6,283,119 B1 | 9/2001 | Bourdon |
| 6,305,373 B1 | 10/2001 | Wallace et al. |
| 6,306,098 B1 | 10/2001 | Orr et al. |
| 6,312,389 B1 | 11/2001 | Kofoed et al. |
| 6,321,748 B1 | 11/2001 | O'Mahoney |
| 6,325,785 B1 | 12/2001 | Babkes et al. |
| 6,325,978 B1 | 12/2001 | Labuda et al. |
| 6,357,438 B1 | 3/2002 | Hansen |
| 6,358,215 B1 | 3/2002 | Ricciardelli |
| 6,360,745 B1 | 3/2002 | Wallace et al. |
| 6,369,838 B1 | 4/2002 | Wallace et al. |
| 6,390,091 B1 | 5/2002 | Banner et al. |
| 6,394,962 B1 | 5/2002 | Gama De Abreu et al. |
| 6,402,697 B1 | 6/2002 | Calkins et al. |
| 6,408,848 B1 | 6/2002 | Feldman et al. |
| 6,412,483 B1 | 7/2002 | Jones et al. |
| 6,439,229 B1 | 8/2002 | Du et al. |
| 6,467,478 B1 | 10/2002 | Merrick et al. |
| 6,471,658 B1 | 10/2002 | Daniels et al. |
| 6,540,689 B1 | 4/2003 | Orr et al. |
| 6,546,930 B1 | 4/2003 | Emerson et al. |
| 6,553,991 B1 | 4/2003 | Isaza |
| 6,557,553 B1 | 5/2003 | Borrello |
| 6,571,795 B2 | 6/2003 | Bourdon |
| 6,575,164 B1 | 6/2003 | Jaffe et al. |
| 6,616,896 B2 | 9/2003 | Labuda et al. |
| 6,622,726 B1 | 9/2003 | Du |
| 6,629,934 B2 | 10/2003 | Mault et al. |
| 6,644,310 B1 | 11/2003 | Delache et al. |
| 6,648,831 B2 | 11/2003 | Orr et al. |
| 6,648,832 B2 | 11/2003 | Orr et al. |
| 6,659,962 B2 | 12/2003 | Ricciardelli |
| 6,668,824 B1 | 12/2003 | Isaza et al. |
| 6,675,801 B2 | 1/2004 | Wallace et al. |
| 6,718,974 B1 | 4/2004 | Moberg |
| 6,725,447 B1 | 4/2004 | Gilman et al. |
| 6,739,337 B2 | 5/2004 | Isaza |
| 6,761,167 B1 | 7/2004 | Nadjafizadeh et al. |
| 6,761,168 B1 | 7/2004 | Nadjafizadeh et al. |
| 6,763,829 B2 | 7/2004 | Jaffe et al. |
| 6,802,225 B2 | 10/2004 | Shahar et al. |
| 6,814,074 B1 | 11/2004 | Nadjafizadeh et al. |
| 6,815,211 B1 | 11/2004 | Blazewicz et al. |
| 6,840,906 B2 | 1/2005 | Gama De Abreu et al. |
| 6,866,040 B1 | 3/2005 | Bourdon |
| 6,908,438 B2 | 6/2005 | Orr et al. |
| 6,954,702 B2 | 10/2005 | Pierry et al. |
| 6,955,651 B2 | 10/2005 | Kück et al. |
| 6,960,854 B2 | 11/2005 | Nadjafizadeh et al. |
| 6,990,980 B2 | 1/2006 | Richey, II |
| 7,004,168 B2 | 2/2006 | Mace et al. |
| 7,018,340 B2 | 3/2006 | Jaffe et al. |
| 7,032,463 B2 | 4/2006 | Misholi et al. |
| 7,036,504 B2 | 5/2006 | Wallace et al. |

(56) References Cited

U.S. PATENT DOCUMENTS

| | | |
|---|---|---|
| 7,066,176 B2 | 6/2006 | Jaffe et al. |
| 7,074,196 B2 | 7/2006 | Kück et al. |
| 7,077,131 B2 | 7/2006 | Hansen |
| RE39,225 E | 8/2006 | Isaza et al. |
| 7,089,930 B2 | 8/2006 | Adams et al. ............... 18/201.27 |
| 7,101,341 B2 | 9/2006 | Tsukashima et al. ......... 600/532 |
| 7,117,438 B2 | 10/2006 | Wallace et al. |
| 7,135,001 B2 | 11/2006 | Orr et al. |
| 7,183,552 B2 | 2/2007 | Russell |
| 7,270,126 B2 | 9/2007 | Wallace et al. |
| 7,291,851 B2 | 11/2007 | DelFavero et al. |
| 7,297,120 B2 | 11/2007 | Tsukashima et al. ......... 600/532 |
| 7,335,164 B2 | 2/2008 | Mace et al. |
| 7,341,563 B2 | 3/2008 | Rich et al. |
| 7,347,205 B2 | 3/2008 | Levi |
| 7,369,757 B2 | 5/2008 | Farbarik |
| 7,370,650 B2 | 5/2008 | Nadjafizadeh et al. |
| 7,427,269 B2 | 9/2008 | George et al. |
| 7,428,902 B2 | 9/2008 | Du et al. |
| 7,432,508 B2 | 10/2008 | Daniels et al. |
| 7,460,959 B2 | 12/2008 | Jafari |
| 7,487,773 B2 | 2/2009 | Li |
| 7,509,957 B2 | 3/2009 | Duquette et al. |
| 7,607,360 B2 | 10/2009 | Todokoro et al. |
| 7,654,802 B2 | 2/2010 | Crawford, Jr. et al. |
| 7,658,891 B1 | 2/2010 | Barnes ..................... 422/186.03 |
| 7,694,677 B2 | 4/2010 | Tang |
| 7,717,113 B2 | 5/2010 | Andrieux |
| 7,721,736 B2 | 5/2010 | Urias et al. |
| D618,356 S | 6/2010 | Ross |
| 7,784,461 B2 | 8/2010 | Figueiredo et al. |
| 7,823,588 B2 | 11/2010 | Hansen |
| 7,855,716 B2 | 12/2010 | McCreary et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| D638,852 S | 5/2011 | Skidmore et al. |
| 7,984,714 B2 | 7/2011 | Hausmann et al. |
| 7,985,254 B2 | 7/2011 | Tolkowsky ........................ 623/9 |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 * | 5/2012 | Perine et al. .............. 128/204.18 |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2001/0029339 A1 | 10/2001 | Orr et al. |
| 2001/0031928 A1 | 10/2001 | Orr et al. |
| 2002/0116994 A1 * | 8/2002 | Heinonen ....................... 73/196 |
| 2002/0128566 A1 | 9/2002 | Gama De Abreu et al. |
| 2003/0047188 A1 | 3/2003 | Mace et al. |
| 2003/0191405 A1 | 10/2003 | Rich et al. |
| 2004/0015058 A1 | 1/2004 | Besson et al. ................ 600/301 |
| 2004/0087867 A1 | 5/2004 | Gama De Abreu et al. |
| 2004/0186391 A1 | 9/2004 | Pierry et al. |
| 2004/0256560 A1 | 12/2004 | Russell |
| 2005/0039748 A1 | 2/2005 | Andrieux |
| 2005/0139212 A1 | 6/2005 | Bourdon |
| 2005/0217275 A1 | 10/2005 | Hendrickson et al. ........... 60/775 |
| 2005/0279358 A1 | 12/2005 | Richey, II |
| 2005/0285055 A1 | 12/2005 | DelFavero et al. |
| 2006/0009707 A1 | 1/2006 | Daniels et al. |
| 2006/0052950 A1 | 3/2006 | Pierry et al. |
| 2006/0086357 A1 | 4/2006 | Soliman et al. |
| 2006/0129054 A1 | 6/2006 | Orr et al. |
| 2006/0145078 A1 | 7/2006 | Russell |
| 2006/0241508 A1 | 10/2006 | Jaffe et al. |
| 2006/0249153 A1 | 11/2006 | DeVries et al. |
| 2006/0253038 A1 | 11/2006 | Kuck et al. |
| 2007/0017515 A1 | 1/2007 | Wallace et al. |
| 2007/0044798 A1 | 3/2007 | Levi |
| 2007/0077200 A1 | 4/2007 | Baker |
| 2007/0107728 A1 | 5/2007 | Ricciardelli et al. |
| 2007/0142716 A1 | 6/2007 | Biondi |
| 2007/0149891 A1 | 6/2007 | George et al. |
| 2007/0157930 A1 | 7/2007 | Soliman et al. |
| 2007/0199566 A1 | 8/2007 | Be'eri |
| 2007/0227537 A1 | 10/2007 | Bemister et al. |
| 2007/0272241 A1 | 11/2007 | Sanborn et al. |
| 2007/0272242 A1 | 11/2007 | Sanborn et al. |
| 2007/0273887 A1 | 11/2007 | Russell |
| 2007/0282214 A1 | 12/2007 | George et al. |
| 2007/0284361 A1 | 12/2007 | Nadjafizadeh et al. |
| 2008/0021339 A1 | 1/2008 | Gabriel et al. ................. 600/532 |
| 2008/0053441 A1 | 3/2008 | Gottlib et al. |
| 2008/0058667 A1 | 3/2008 | Pierry et al. |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0091117 A1 | 4/2008 | Choncholas et al. |
| 2008/0092894 A1 | 4/2008 | Nicolazzi et al. |
| 2008/0092898 A1 * | 4/2008 | Schneider et al. ....... 128/206.28 |
| 2008/0097234 A1 | 4/2008 | Nicolazzi et al. |
| 2008/0119753 A1 | 5/2008 | Ricciardelli et al. |
| 2008/0177404 A1 | 7/2008 | Bonnat ............................ 700/90 |
| 2008/0200776 A1 | 8/2008 | Schermeier et al. .......... 600/301 |
| 2009/0044805 A1 * | 2/2009 | Somaiya et al. .......... 128/204.22 |
| 2009/0165795 A1 | 7/2009 | Nadjafizadeh et al. |
| 2009/0171176 A1 | 7/2009 | Andersohn |
| 2009/0205661 A1 | 8/2009 | Stephenson et al. |
| 2009/0205663 A1 | 8/2009 | Vandine et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2009/0320842 A1 | 12/2009 | Doherty et al. .......... 128/204.21 |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0139660 A1 | 6/2010 | Adahan |
| 2010/0147303 A1 | 6/2010 | Jafari et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0282259 A1 | 11/2010 | Figueiredo et al. |
| 2010/0288283 A1 | 11/2010 | Campbell et al. |

(56) References Cited

U.S. PATENT DOCUMENTS

| | | |
|---|---|---|
| 2010/0300446 A1 | 12/2010 | Nicolazzi et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandine et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0162647 A1 | 7/2011 | Huby et al. ............ 128/203.14 |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0304995 A1 | 12/2012 | Kauc |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0025596 A1 | 1/2013 | Jafari et al. |
| 2013/0025597 A1 | 1/2013 | Doyle et al. |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0167842 A1 | 7/2013 | Jafari et al. |
| 2013/0167843 A1 | 7/2013 | Kimm et al. |
| 2013/0192599 A1 | 8/2013 | Nakai et al. |
| 2013/0220324 A1 | 8/2013 | Jafari et al. |
| 2013/0255682 A1 | 10/2013 | Jafari et al. |
| 2013/0255685 A1 | 10/2013 | Jafari et al. |
| 2013/0284172 A1 | 10/2013 | Doyle et al. |

FOREIGN PATENT DOCUMENTS

| | | | |
|---|---|---|---|
| JP | 2002136595 | 5/2002 | |
| WO | 9004425 | 5/1990 | ............ A61M 16/00 |
| WO | WO 96/41571 | 12/1996 | |

OTHER PUBLICATIONS

"Puritan Bennett CPAP/BiLevel Tubing with Internal Pressure Sensor Line", Printout of page from website www.cpapxchange.com, 2 pages, Printed Jun. 9, 2010.

International PCT Search Report and Written Opinion, PCT/US2009/055288, 17 pages, Mailed Dec. 4, 2009.

Application for Letters Patent, "System and Process for Supplying Respiratory Gas Under Pressure or Volumetrically," Inventor Claude Andreiux, 21 pages, Filed Jul. 27, 2004.

7200 Series Ventilator, Options, and Accessories: Operator's Manual. Nellcor Puritan Bennett, Part No. 22300 A, Sep. 1990, pp. 1-196.

7200 Ventilatory System: Addendum/Errata. Nellcor Puritan Bennett, Part No. 4-023576-00, Rev. A, Apr. 1998, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

\* cited by examiner

SYSTEMS AND METHODS FOR MANAGING PRESSURE IN A BREATHING ASSISTANCE SYSTEM

CROSS-REFERENCE TO RELATED APPLICATIONS

This application is a continuation of U.S. patent application Ser. No. 12/238,607 (now U.S. Pat. No. 8,181,648) filed Sep. 26, 2008 now U.S. Pat. No. 8,181,648, the contents of which is incorporated herein by reference in its entirety.

TECHNICAL FIELD

The present disclosure is related to systems and methods for managing pressure in a breathing assistance system, e.g., a ventilator or continuous positive airway pressure (CPAP) device.

BACKGROUND

Breathing assistance systems such as ventilators and Continuous Positive Airway Pressure (CPAP) devices are used to provide various types of breathing assistance to patients. Typically, a patient is connected to a breathing assistance system by a connection system, which may include, for example, a patient circuit, a mask, nasal pillows, tracheal tube, and/or other conduits and connection devices. A CPAP device may be used for treatment of obstructive sleep apnea syndrome. Such a device may deliver pressurized air to the patient, which keeps the patient's upper airways from collapsing during sleep. In some breathing assistance systems, data regarding the pressure delivered to the patient, or the pressure at the patient end of the connection system, is useful to the breathing assistance system, e.g., as feedback to the system or as an input for controlling the operation of the system.

When delivering gas to a patient via a patient connection system, it is often useful or necessary to measure or determine the pressure near the patient end of the connection system (e.g., patient circuit). However, it is often difficult or impractical to measure the pressure near the patient end of the connection system, e.g., due to extra costs, tubing, and/or other practical concerns associated with providing a pressure sensor near the patient end of the connection system. Thus, the pressure may be measured near the gas delivery device of the breathing assistance system (e.g., the ventilator system or CPAP box). For example, a pressure sensor may be located just outside or within the housing of the ventilator or CPAP box. However, the pressure measured near the gas delivery device (i.e., remote from the patient end of the connection system) may not provide the most accurate data regarding the actual pressure at the patient end of the connection system, based at least in part on pressure drop effects inherent in a patient connection system.

SUMMARY

According to one embodiment of the present disclosure, a breathing assistance system for providing breathing assistance to a patient is provided. The breathing assistance system may include a ventilation system for supplying a gas flow, a patient connection device for connection to the patient, a conduit operatively coupled between the ventilation system and the patient connection device, and a pressure sensor configured to measure the pressure of the gas flow through the conduit. The pressure sensor may include a structure configured to create a localized pressure drop in the gas flow proximate the pressure sensor structure.

According to another embodiment of the present disclosure, a pressure sensor for use in a breathing assistance system for providing breathing assistance to a patient is provided. The pressure sensor may include a pressure sensor structure extending at least partially into an interior of a conduit operatively coupled between a ventilation system configured to supply a gas flow and a patient connection device configured for connection to the patient. The pressure sensor structure may be configured to affect the gas flow in the conduit to create a localized pressure drop proximate the pressure sensor structure. The pressure sensor may further include a gas inlet formed in the pressure sensor structure, the gas inlet configured to receive gas for pressure measurement.

According to another embodiment of the present disclosure, a method for controlling pressure delivered to a patient of a breathing assistance system is provided. The method may include determining a target pressure setting and controlling a gas delivery device to generate a gas flow toward a patient based at least on the target pressure setting. The method may further include receiving pressure measurements from a pressure sensor operatively coupled to a conduit between the gas delivery device and the patient, the pressure sensor including a structure configured to create a localized pressure drop in the gas flow proximate the pressure sensor structure. The method may further include adjusting the gas delivery device based at least on the pressure measurements received from the pressure sensor.

Certain embodiments are generally directed toward a pressure sensor that may be located remote from a patient, yet usable for accurately controlling the pressure delivered to the patient. For example, the pressure sensor may be located near an end of a patient circuit near the ventilation system (e.g., ventilator housing or CPAP box), as opposed to an end of the patient circuit near the patient.

In some embodiments, the structure of the pressure sensor produces a localized pressure drop near the pressure sensor (at least during positive flow toward the patient) that may approximate or simulate a pressure drop in the gas flow that naturally occurs as the gas flows along the length of the patient circuit. Thus, the pressure measured by the pressure sensor located remote from the patient may approximate the pressure actually at or near the patient. A gas delivery control system may use pressure measurements form such a pressure sensor to accurately control the pressure delivered to the patient. In this manner, a pressure sensor according to certain embodiments of the present disclosure may be used to automatically compensate for the pressure drop in the patient circuit.

BRIEF DESCRIPTION OF THE DRAWINGS

Some embodiments of the disclosure may be understood by referring, in part, by way of example, to the following description and the accompanying drawings, in which like reference numbers refer to the same or like parts and wherein.

DETAILED DESCRIPTION

Selected embodiments of the disclosure may be understood by reference, in part, to FIGS. 1-7, wherein like numbers refer to same and like parts. The present disclosure relates generally to measuring pressure in a breathing assistance system, including compensating for pressure drop in the system. As known in the field, when delivering gas to a patient via a patient connection system (e.g., a mask and a patient circuit), the pressure measured near the outlet of the gas delivery system (e.g., a blower, a ventilator or a CPAP box) may not provide accurate data regarding the actual pressure delivered to the patient, based at least in part on the inherent pressure drop as the gas flow through the patient circuit or other conduit toward the patient. In particular, due to such inherent pressure drop, the pressure measured near the outlet of the gas delivery system is typically greater than the actual pressure delivered to the patient during positive air flow (toward the patient). Similarly, the pressure measured near the outlet of the gas delivery system is typically lower than the actual pressure delivered to the patient during negative air flow (away from the patient).

However, it is often necessary or desirable to measure the pressure near the outlet of the gas delivery, system rather than at the patient end of the patient connection system. Accordingly, the present disclosure provides a pressure sensor that may be located near the outlet of the gas delivery system and used by a gas delivery control system to compensate for the pressure drop in the patient circuit. In particular, the pressure sensor may have a structure that produces a localized pressure drop near the pressure sensor that may approximate, or simulate, the pressure drop of gas flow through the length of the patient circuit. Thus, the pressure measured by the pressure sensor may approximate the actual pressure delivered to the patient. A gas delivery control system may thus use these pressure measurements to accurately control the pressure delivered to the patient. In this manner, a pressure sensor according to certain embodiments of the present disclosure may be used to automatically compensate for the pressure drop in the patient circuit.

Figure 1:
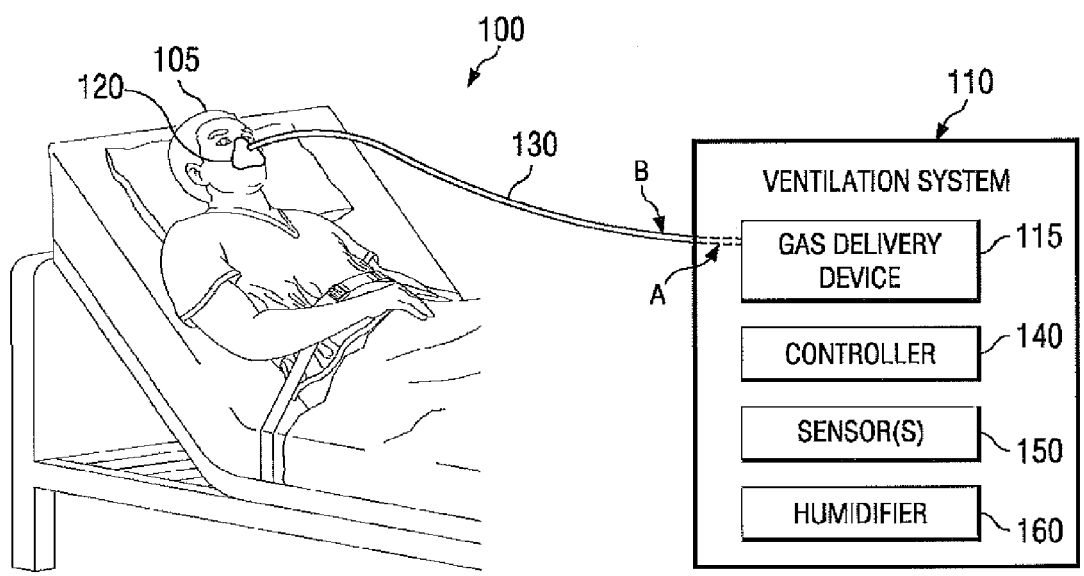
FIG. 1 illustrates an example breathing assistance system for communicating gas to and/or from a patient, according to certain embodiments of the present disclosure.

FIG. 1 illustrates an example breathing assistance system 100 for communicating gas to and/or from a patient 105, according to certain embodiments of the present disclosure. Breathing assistance system 100 may be generally configured to provide breathing assistance to a patient 105 (e.g., providing ventilation and/or treating an apnea or other breathing condition of the patient). Breathing assistance system 100 may include a ventilation system 110, a patient connection device 120, and a patient circuit 130 between ventilation system 110 and patient connection device 120. Ventilation system 110 may comprise any device for providing breathing assistance to patient 105, e.g., a ventilator, respirator, CPAP device, or Bilevel Positive Airway Pressure (BiPAP) device. Ventilation system 110 may include a gas delivery device 115, a controller 140, one or more sensors 150, a humidifier 160, user interfaces, a display system, and any other suitable components.

Gas delivery device 115 may be configured to generate, supply, and/or deliver gas toward patient 105. For example, gas delivery device 115 may comprise a device capable of generating pressurized air (e.g., a motorized blower or piston-based device), a wall outlet through which pressurized air may be supplied (e.g., in a hospital or clinic), valves configured to control the supply of gas to patient 105 (e.g., a PSOL or other solenoid valve), one or more tanks of compressed gas, a compressor, or any other suitable source of pressurized or non-pressurized gas.

In some embodiments, ventilation system 110, in cooperation with other components of breathing assistance system 100 (e.g., an exhalation valve), may generate both positive gas flow (toward patient 105) and negative gas flow (away from patient 105). For example, a positive gas flow may be generated as gas is delivered to patient 105 during inhalation, while a negative gas flow may be generated as exhaust gas is communicated from patient 105 during exhalation. In other embodiments, ventilation system 110 may be configured to generate only positive or negative gas flow.

As used herein, the term "gas" may refer to any one or more gases and/or vaporized substances suitable to be delivered to and/or from patient 105 via one or more breathing orifices (e.g., the nose and/or mouth), such as air, nitrogen, oxygen, any other component of air, $CO_2$, vaporized water, vaporized medicines, and/or any combination of two or more of the above, for example.

As used herein, the term "patient" may refer to any person or animal that may receive breathing assistance from system 100, regardless of the medical status, official patient status, physical location, or any other characteristic of the person. Thus, for example, patients may include persons under official medical care (e.g., hospital patients); persons not under official medical care; persons receiving care at a medical care facility; persons receiving home care; etc.

Patient circuit 130 may be generally configured to deliver gas from ventilation system 110 toward patient 105 and/or to communicate exhaust gas away from patient 105. For example, patient circuit 130 may comprise any suitable type of breathing circuit, e.g., a single-limb or dual-limb circuit. As a particular example, patient circuit 130 may include an approximately 1.8 m long tube with a diameter of about 22 mm. Patient circuit 130 may be connected at one end to ventilation system 110 and at another end to patient connection device 120.

Patient connection device 120 is generally configured to connect patient circuit 130 to one or more breathing passageways of patient 105. For example, patient connection device 120 may comprise an artificial airway (e.g., an endotracheal tube or other device) inserted in the patient's trachea, or a nasal mask, face mask, nasal pillows, or any other patient interface for communicating gas to and/or from the patient's nose and/or mouth.

Depending on various factors including the gas flow rate, the resistance of patient circuit 130, and/or the resistance of patient connection device 120, the actual gas pressure at patient 105 or patient connection device 120 may be different from the controlled or measured pressure at or near ventilation system 110 (e.g., within a housing of ventilation system 110 or at an end of connection system 130 near ventilation system 110). For example, during inhalation (positive gas flow), the gas pressure at patient connection device 120 may be less than the regulated or measured pressure at or near ventilation system 110 because the inherent resistance of patient circuit 130 may cause a pressure drop along the length of patient circuit 130, with the amount of pressure drop being a function of gas flow. Similarly, during exhalation (negative gas flow), the gas pressure at patient connection device 120 may be higher than the regulated or measured pressure at or near ventilation system 110 again due to the pressure drop along the length of patient circuit 130 caused by the inherent resistance of patient circuit 130.

Controller 140 may be operable to control gas delivery device 115 and/or other system components to control the delivery of gas toward and/or away from patient 105 based on, for example, various input received from a user (e.g., via a touch screen and/or other user interfaces) and/or data received from one or more sensors 150. For example, controller 140 may regulate the pressure and/or flow rate of gas delivered toward and/or away from patient 105 based at least on pressure and/or flow data received from sensors 150.

Controller 140 may include, or have access to, one or more processors, memory devices, and any other suitable hardware, software, and/or firmware. The memory devices may store instructions (e.g., any suitable software, algorithms, or other logic or instructions that may be executed by one or more processors) for automatically controlling the operation of ventilation system 110 (e.g., controlling the pressure and/or flow rate) based various input data.

One or more sensors 150 may be provided for sensing, detecting, and/or monitoring one or more parameters related to the ventilation of patient 105, e.g., parameters regarding the ventilation provided by ventilation system 110 and/or physiological parameters regarding patient 105. For example, sensors 150 may include one or more devices for measuring various parameters of gas flowing to or from patient 105 or ventilation system 110, e.g., the pressure, flow rate, flow volume, temperature, gas content, and/or humidity of such gas flow.

In certain embodiments, sensors 150 may include a pressure sensor located at any suitable location in breathing assistance system 100. For example, pressure sensor 150 may be integrated with or coupled to ventilation system 110, integrated with or coupled to patient circuit 130, or otherwise associated with breathing assistance system 100.

In certain embodiments, pressure sensor 150 may be located at or near a gas outlet of ventilation system 110. For example, pressure sensor 150 may be located inside or just outside a housing or enclosure of ventilation system 110, or at an end of connection system 130 near ventilation system 110). Pressure sensor 150 may be positioned to measure the pressure of gas flow exiting ventilation system 110, as generally indicated by arrow A in FIG. 1, or the pressure of gas flow entering patient circuit 130, as generally indicated by arrow B in FIG. 1. According to certain embodiments, pressure sensor 150 may be located at the opposite end of patient circuit 130 from patient 105.

In some embodiments or configurations, breathing assistance system 100 may include a humidifier 160, which may be integral with or separate from, ventilation system 110. Humidifier 160 may be located and connected to breathing assistance system 100 in any suitable manner. Humidifier 160 is typically located between gas delivery device 115 and patient 105. In some embodiments, humidifier 160 is located downstream of pressure sensor 150, and may affect (e.g., increase) the pressure drop between pressure sensor 150 and patient 105 along patient circuit 130. Humidifier 160 may include any known type of humidifier for use with a ventilator, CPAP system, or other type of breathing assistance system 100.

User interfaces of breathing assistance system 100 may include any suitable device or devices allowing a user to interface with breathing assistance system 100, e.g., to control ventilation system 110, to navigate through various display screens, to make selections, and/or to set, modify, or otherwise control various parameters regarding breathing assistance system 100. For example, user interfaces may allow a user to input desired performance parameters (e.g., pressure or flow rate) that may be communicated to controller 140 to control the operation of ventilation system 110 and/or other components of breathing assistance system 100. In some embodiments, system 100 may include a graphic user interface (GUI), one or more manual input devices separate from the GUI, and/or any other input devices. The GUI may include a touch screen configured to display various information and provide an interface for accepting input from user (e.g., to navigate through various screens, to make selections, to set or modify various parameters, to change or configure the display, etc.). Manual input devices may include any physical buttons, knobs, dials, switches, levers, or any other devices that may be manipulated by a user.

Breathing assistance system 100 may include a display device. The display device may comprise a screen or any other device suitable for visually displaying medical data. For example, the display device may include a monitor, a Liquid Crystal Display (LCD) screen, light emitting diodes (LEDs), or any other visual device. In some embodiments, the display device and user interfaces may be at least partially integrated, e.g., where ventilation system 110 includes a touch screen or other GUI.

Figure 2:
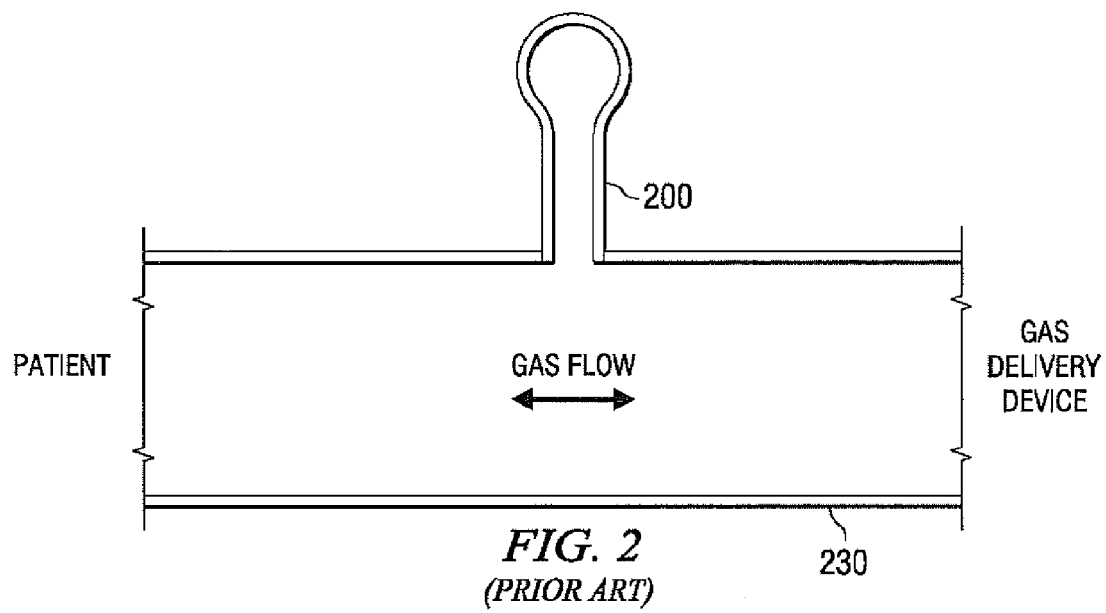
FIG. 2 illustrates an example configuration of a known pressure sensor in a breathing assistance system.

FIG. 2 illustrates a typical configuration of a pressure sensor 200 in a patient circuit 230 or other conduit, according to the prior art. Pressure sensor 200 comprises an opening extending perpendicular to the direction of gas flow between the ventilation system and the patient. A pressure sensor configured in this manner—perpendicular to the gas flow—may generally accurately measure pressure at the location of the sensor, but not accurately measure the pressure at a distance from the sensor along the gas flow path, e.g., due to pressure drop effects discussed herein. Thus, for example, a pressure sensor configured as pressure sensor 200 shown in FIG. 2 and located at the ventilation system end of patient circuit 230 will generally not accurately measure the pressure at the patient end of patient circuit 230. As discussed above, depending on factors including the gas flow rate and on the resistance of patient circuit 230, the pressure actually delivered to patient connection may be different from the regulated pressure at the ventilation system. For example, if the gas flow is positive (toward patient 105), the pressure delivered to the patient may be lower than the regulated or measured pressure at the ventilation system due to pressure drop in patient circuit 230 and/or other conduits. As another example, during the expiratory phase of the breath, the gas flow is negative (away from patient 105) and the pressure at patient connection may be higher than the regulated pressure at the ventilation system.

Figure 3:
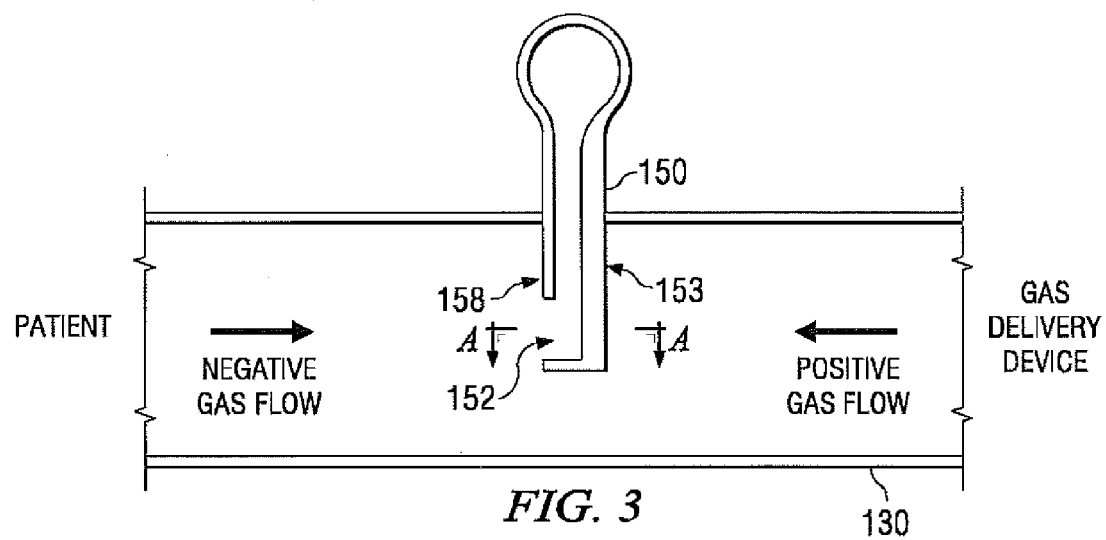
FIG. 3 illustrates an example configuration of a pressure sensor for use in the breathing assistance system of FIG. 1, according to certain embodiments of the present disclosure.

FIG. 3 illustrates an example pressure sensor 150 for use in breathing assistance system 100 of FIG. 1, according to certain embodiments of the present disclosure. Pressure sensor 150 may be located at any suitable location in breathing assistance system 100, e.g., at or near the ventilation system end of patient circuit 130. Pressure sensor 150 may be formed from any suitable material(s), e.g., plastic, and may include polished surfaces.

As shown in FIG. 3 (as well as FIG. 4), the gas intake of example pressure sensor 150, indicated at 152, is aligned with the direction of gas flow through patient circuit 130. With such orientation, the measurements provided by pressure sensor 150 depend on the gas flow rate, as well as the direction of the gas flow. Generally, the greater the flow rate, the greater the difference in pressure measurements provided by pressure sensor 150 oriented as shown in FIG. 3 as compared to pressure sensor 200 oriented as shown in FIG. 2. If there is no gas flow, the measurements provided by pressure sensor 150 of FIG. 3 and pressure sensor 200 of FIG. 2 are generally the same.

As shown in FIG. 3, pressure sensor 150 may define an intake side 158 and a leading side 153 generally opposite intake side 158. During positive gas flow, shown in FIG. 3 as flow to the left, leading side 153 of pressure sensor 150 may generate a drop in pressure at gas intake 152 of pressure sensor 150. For example, leading side 153 of pressure sensor 150 may create local turbulence and/or other flow pattern effects for a portion of the flow near pressure sensor 150 that generate a drop in pressure local to gas intake 152 formed in the back side of sensor 150. Thus, the measured pressure may be lower than the pressure of the flow approaching pressure sensor 150, as well as portions of the flow continuing past pressure sensor 150 that are not significantly affected by the structure of pressure sensor 150. In some embodiments, the portion of the flow that is affected by pressure sensor 150 may be relatively minor compared to the overall gas flow passing by pressure sensor 150, such that pressure sensor 150 does not significantly affect the overall gas flow between ventilation system 110 and patient 105.

In some embodiments, the local pressure drop created by the structure of pressure sensor 150 may be configured to approximate or simulate the inherent pressure drop associated with the gas flow through patient circuit 130 (in particular, the inherent pressure drop along the flow path from the particular location of pressure sensor 150 to the patient), such that the pressure measured by pressure sensor 150 during positive flow approximates the actual pressure near patient 105.

During negative gas flow, shown in FIG. 3 as flow to the right, gas entering the intake 152 aligned with the gas flow may generate an overpressure. For example, intake side 158 of pressure sensor 150 may be configured to generate an increase in pressure entering gas intake 152. Thus, the pressure measured by pressure sensor 150 may be higher than the pressure of the flow approaching pressure sensor 150, as well as portions of the flow continuing past pressure sensor 150 that are not significantly affected by the structure of pressure sensor 150.

In some embodiments, the local pressure increase created by the structure of pressure sensor 150 may be configured to approximate in magnitude the inherent pressure drop associated with the gas flow through patient circuit 130 (and in particular, the inherent pressure drop along the flow path from patient 105 to pressure sensor 150), such that the pressure measured by pressure sensor 150 during negative flow approximates the actual pressure near patient 105.

Thus, pressure sensor 150 may produce a localized pressure drop during positive flow and/or a localized pressure increase during negative flow such that the pressure measured by pressure sensor 150 approximates or simulates the actual pressure near patient 105. Ventilation system 110 (e.g., controller 140) may thus use pressure measurements form pressure sensor 150 to relatively accurately control the pressure at patient 105. Thus, pressure sensor 150 may be said to automatically compensate for the pressure drop in the system during positive and/or negative gas flow. In some embodiments, controller 140 may accurately control the pressure at patient 105 based on data from a single pressure sensor 150 located remote from patient 105. In other embodiments, ventilation system 110 may control the pressure delivered to patient 105 based on data from multiple pressure sensors 150 or based on data from a pressure sensor 150 and data from one or more other types of sensors or other sources.

In order for pressure sensor 150 to properly approximate or simulate the pressure drop between ventilation system 110 and patient 105, an appropriate shape, size, and/or configuration of pressure sensor 150 may be selected, e.g., based on computer simulation or actual testing. For example, the leading side 153 of pressure sensor 150 that extends inside patient circuit 130 may be shaped such that during positive gas flow, the structure of pressure sensor 150 generates a drop of pressure equivalent to the drop of pressure between the ventilation system and patient 105 (e.g., the pressure drop along patient circuit 130). Further, the intake side 158 of pressure sensor 150 may be shaped such that during negative gas flow, the structure of pressure sensor 150 generates a pressure increase equivalent to the difference in pressure between the ventilation system and patient 105.

Figure 4:
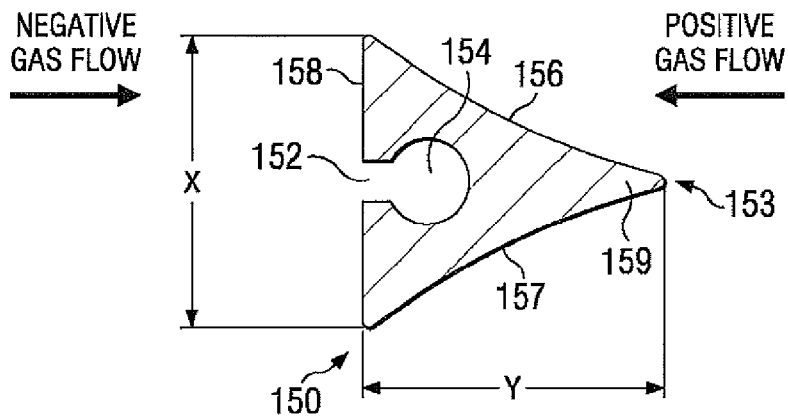
FIG. 4 illustrates an example cross-section of the pressure sensor of FIG. 3 taken along line A-A of FIG. 3, according to one embodiment of the present disclosure.

FIG. 4 illustrates an example cross-section of pressure sensor 150 of FIG. 3 taken along line A-A of FIG. 3, according to one embodiment of the present disclosure. Pressure sensor 150 may define an intake side 158 including intake 152 formed therein for communicating the gas to an opening 154, and a leading side 153. Intake 152 and opening 154 allow gas to enter the pressure sensor 150 for pressure measurement. As shown in FIGS. 3 and 4, intake 152 is aligned in the direction of the gas flow.

The shape, size, and/or orientation of intake side 158, intake 152, and leading side 153 may be selected depending on the pressure drop to be compensated for (e.g., based on the geometry of the patient circuit 130). In the example embodiment shown in FIG. 4, intake side 158 is substantially flat. In other embodiments, intake side 158 may include one or more curved and/or convex portions. In some embodiments, the portions of intake side 158 on each side of intake 152 may be angled inward in order to essentially channel, or funnel, gas flow into intake 152. In the example embodiment shown in FIG. 4, intake side 158 faces patient 105 and is oriented perpendicular to the gas flow. In other embodiments, intake side 158 may be oriented at any other suitable angle relative to the gas flow.

Figure 5:
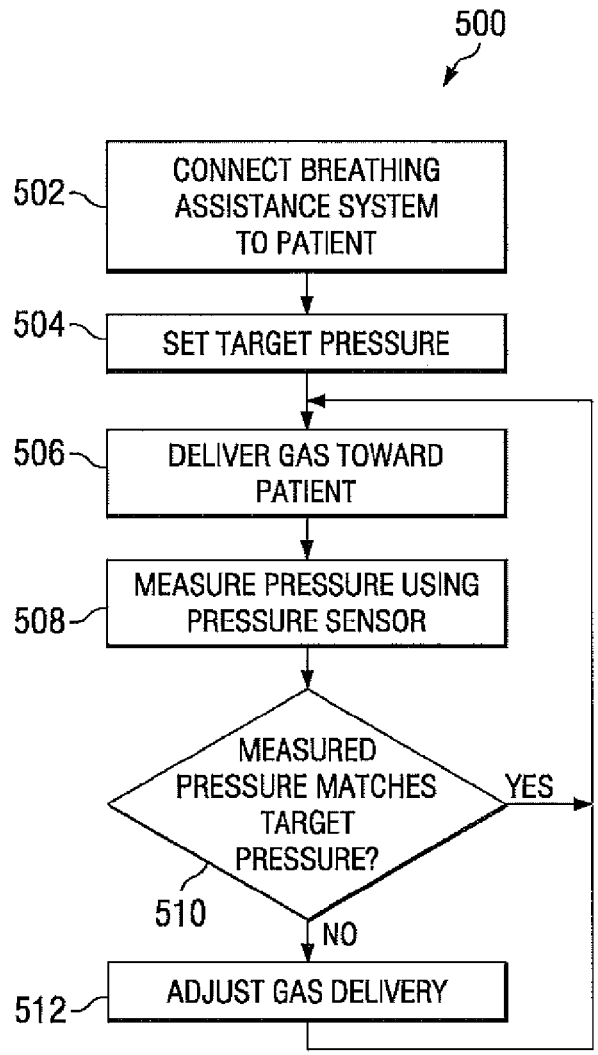
FIG. 5 illustrates a flow chart of an example method of compensating for pressure drop in a breathing assistance system using a pressure sensor according to certain embodiments of the present disclosure.

In the example embodiment shown in FIG. 4, leading side 153 may define a leading protrusion 159 that facing into the positive gas flow direction. Leading protrusion 159 includes two sides 156 and 157 connecting leading protrusion 159 with intake side 158. Sides 156 and 157 may be concave, convex, or straight, or may have any other suitable shape. Leading protrusion 159 may be more or less pointed, or even partly or substantially flat, depending on the particular embodiment. The shape, size, and orientation of leading side 153 (in this embodiment, leading protrusion 159) affects the pressure drop, and thus the pressure measured by sensor 150, during positive gas flow. Generally, the more the shape, size, and orientation of leading side 153 guides the gas flow away from intake 152 and/or creates turbulence in the gas flow, the lower the pressure measured by pressure sensor 150, and thus the greater the pressure drop that can be accounted for. Thus, the shape, size, and orientation of pressure sensor 150 can be configured to correspond to the pressure drop associated with the particular system configuration. If should be clear that the example configuration shown in FIG. 5 is only one example and other configurations may alternatively be used for compensating for various pressure drops. For example, in other example embodiments, pressure sensor 150 may include a substantially T-shaped section.

In some embodiments, the width X of intake side 158 and the length Y of pressure sensor 150 may be substantially equal. For example, for a patient circuit 1.8 m long and 22 mm in diameter, the width X and length Y may both be about 6 mm. In other embodiments, the width X and length Y may have any other similar or different dimensions.

In operation, breathing assistance system 100 may supply gas to patient 105. The gas may be provided from a ventilation system 110 via patient circuit 130 to patient connection device 120. A pressure sensor 150 located near or within the ventilation system 110 may take local pressure measurements. The structure of pressure sensor 150 aligned and configured as described herein may affect the local pressure of gas measured by pressure sensor 150 in order to simulate the pressure drop inherent in patient circuit 130, such that controller 140 may use measurements from pressure sensor 150 to automatically compensate for such pressure drop.

FIG. 5 illustrates a flow chart of an example method 500 of compensating for pressure drop in a breathing assistance system 100 using a pressure sensor 150 according to certain embodiments of the present disclosure. In certain embodiments, method 500 includes use of a pressure sensor 150 aligned with a direction of the gas flow and configured such that the configuration alone compensates for a pressure drop within breathing assistance system 100.

According to certain embodiments, method 500 preferably begins at step 502. As noted above, teachings of the present disclosure may be implemented in a variety of configurations of system 100. As such, the preferred initialization point for method 500 and the order of the steps 502-512 comprising method 500 may depend on the implementation chosen.

At step 502, patient 105 is connected to breathing assistance system 100. In particular, a connection device 120 may be connected to patient 105. System 100 may include a pressure sensor 150 arranged to be aligned with a flow direction of the gas, e.g., as described above with reference to FIGS. 3 and 4. Pressure sensor 150 may be located at any suitable location, including within or near the housing of ventilation system 110, e.g., within an end of patient circuit 130 opposite the patient 105.

At step 504, controller 140 may determine a target pressure and/or any other target parameter(s) for gas delivery to patient 105. A target pressure may be determined in any suitable manner, e.g., selected manually by a user or automatically by controller 140 or other component of ventilation system 110. The target pressure may be a desired pressure to be delivered to patient 105.

At step 506, gas delivery device 115 of ventilation system 110 may deliver gas toward patient 105 (i.e., positive flow) via patient circuit 130 and connection device 120. Gas delivery device 115 may be controlled by controller 140, e.g., based on the target pressure and/or any other target parameter(s) determined at step 504.

At step 508, pressure sensor 150 may take one or more pressure measurements. As discussed above, due to the shape and configuration of pressure sensor 150, the local pressure measured by pressure sensor 150 is lower than the pressure of gas passing by and not significantly affected by pressure sensor 150. For example, pressure sensor 150 may be designed such that the local pressure measured by pressure sensor 150 approximates or simulates the actual pressure of gas delivered to patient 105. Pressure sensor 150 may communicate its pressure measurements to controller 140 as any suitable type of data signals.

At step 510, controller 140 may compare the pressure measurement(s) taken by pressure sensor 150 at step 508 with the target pressure determined at step 504. Where multiple pressure measurements are taken at step 508, controller 140 may analyze such pressure measurements in any suitable manner, e.g., by calculating an arithmetic mean or median value.

If the pressure measured by pressure sensor 150 matches the target pressure, the method may return to 506 and gas delivery device 115 may continue to deliver gas at the same flow rate.

Alternatively, if the pressure measured by pressure sensor 150 does not match the target pressure, controller 140 may control gas delivery device 115 accordingly at step 512. For example, if the pressure measured by pressure sensor 150 is lower than the target pressure 150, controller 140 may control gas delivery device 115 to increase the flow rate (e.g., by increasing a motor or blower speed in certain embodiments). Similarly, if the pressure measured by pressure sensor 150 is higher than the target pressure 150, controller 140 may control gas delivery device 115 to decrease the flow rate (e.g., by decreasing a motor or blower speed in certain embodiments).

In some embodiments, controller may determine whether the pressure measured by pressure sensor 150 "matches" the target pressure by determining whether the difference falls within a threshold amount. Such threshold amount may be determined in any suitable manner, e.g., selected manually by a user or automatically set and/or controlled by controller 140. For example, the threshold may be automatically set at a particular value or may be a percentage of the current target pressure. The threshold may be either static or (manually or automatically) adjusted over time.

Gas delivery device 115 may then continue to deliver gas at the adjusted flow rate, as indicated at step 506.

As discussed above, the pressure measured by pressure sensor 150 may approximate or simulate the actual pressure delivered to patient 105, as the size, shape, and/or configuration of pressure sensor 150 may cause a local pressure drop that approximates or simulates the pressure drop experienced along the length of patient circuit 130. Thus, at least during periods of relative stability or equilibrium (e.g., infrequent or minor adjustments to gas delivery device 115), the pressure delivered to patient 105 may approximate the target pressure to be delivered to patient 105 (e.g., manually or automatically set at step 504).

Method 500 may be implemented using any suitable system, e.g., breathing assistance system 100. In addition, method 500 may include any additional steps or may omit one or more steps. The steps of method 500 may be preformed in any suitable order and with any suitable frequency. For example, steps 508-512 may be performed multiple times during a single inhalation or breath, or once per inhalation or breath, or at periodic intervals longer than a breath cycle.

In some embodiments or situations, ventilation system 110 may also provide or allow for periods of negative flow (i.e., flow away from patient 105) through patient circuit 130. For example, negative flow may occur during exhalation (as opposed to positive flow during inhalation). In such embodiments, controller 140 may store a negative flow target pressure, which may be different (e.g., lower) than the positive flow target pressure discussed above at steps 504-510. During negative flow, pressure sensor 150 may take and communicate pressure measurements to controller 140. Controller 140 may then compare the measured pressure to the negative flow target pressure and adjust gas delivery device 115 accordingly, e.g., in a similar manner as discussed above at steps 506-512.

Figure 6:
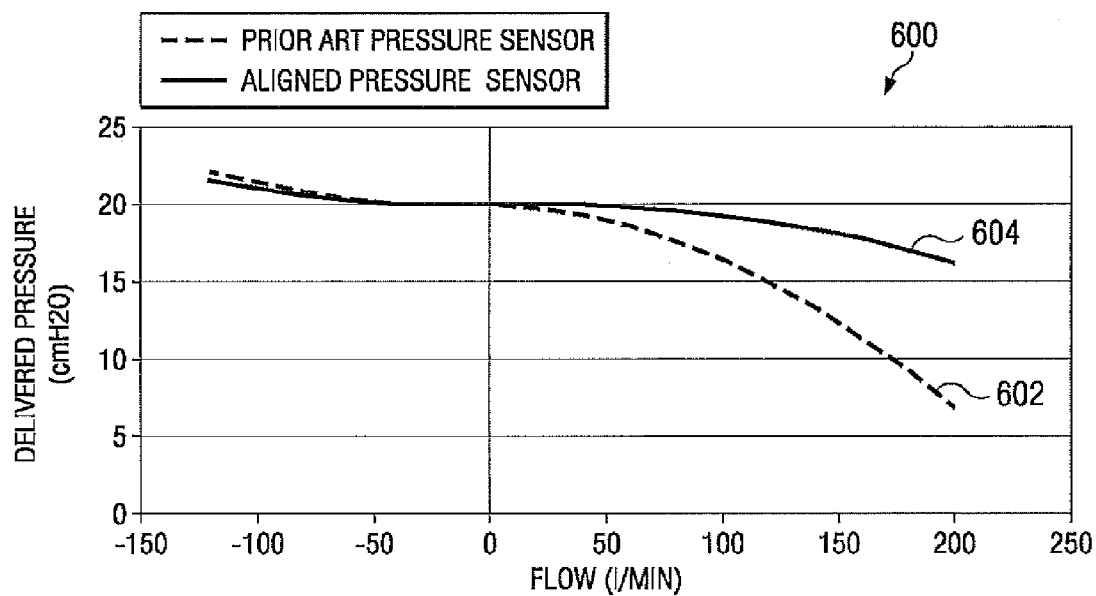
FIG. 6 illustrates a graph of delivered air pressure vs. air flow through a patient connection system for (a) a prior art pressure sensor and (b) an example pressure sensor according to the present disclosure.

FIG. 6 illustrates a graph 600 of pressure of gas delivered to patient 105 versus the flow rate of the delivered gas, according to certain embodiments. The horizontal axis indicates flow rate, in liters per minute. The vertical axis indicates the pressure delivered to patient 105, in cmH$_2$O. The unit cmH$_2$O is normally used in the field of breathing assistance systems and can easily be changed to the SI unit Pascal by multiplying each cmH$_2$O with a factor of 9.81. (For example: 20 cmH$_2$O≈1960 Pa.).

A first plot 602 indicates the actual pressure delivered to patient 105 using a system controlled based on pressure measurements from a pressure sensor configured according to the prior art, e.g., pressure sensor 200 shown in FIG. 2. A second plot 604 indicates the actual pressure delivered to patient 105 using a system controlled based on pressure measurements from a pressure sensor configured according to certain embodiments of the present disclosure, e.g., pressure sensor 150 shown in FIGS. 3-4, which is indicated in FIGS. 6 and 7 as an "aligned pressure sensor" as the opening 152 of pressure sensor 150 is aligned in the same direction as the gas flow path (at least in certain embodiments).

For both plots, the target pressure setting is 20 cmH$_2$O, as shown in FIG. 6 at a flow rate of 0 liters/min. As shown in FIG. 6, for flow rates above 0, the actual pressure delivered to patient 105 in the system controlled based on the prior art pressure sensor (indicated by line 602) is lower, and further from the target pressure setting is 20 cmH$_2$O, than in the system controlled based on a pressure sensor (e.g., sensor 150) of the present disclosure. Thus, the error associated with the system controlled based on the prior art pressure sensor (e.g., due to pressure drop inherent in the system) is greater than the error associated with the system controlled based on pressure sensor 150 of the present disclosure. Further, the error magnitude is a function of flow rate. As the flow rate increases, the difference in the actual delivered pressure between the two systems increases, as shown in FIG. 6. Thus, the error associated with the system controlled based on the prior art pressure sensor becomes further magnified as the flow rate increases.

In this example graph, the error associated with pressure sensor 150 is significantly smaller than the error associated with prior art pressure sensors, particularly at higher flow rates. The particular plot line 604 is a function of the particular size, shape, configuration, and/or other parameters of the particular pressure sensor 150. Thus, the size, shape, configuration, and/or other parameters of the pressure sensor 150 may be adjusted or designed as desired to produce desired results (e.g., a desired plot line 604). For example, other embodiments of pressure sensor 150 may provide an actual delivered pressure that is even closer to the target pressure setting. Thus, the magnitude of error in the system may be controlled by selecting the particular size, shape, configuration, and/or other parameters of the particular pressure sensor 150. In some embodiments, pressure sensor 150 may be configured such that a system controlled based on measurements from pressure sensor 150 delivers gas to patient 105 that is equal to, or even higher than, the target pressure setting, even at relatively high operational flow rates.

Figure 7:
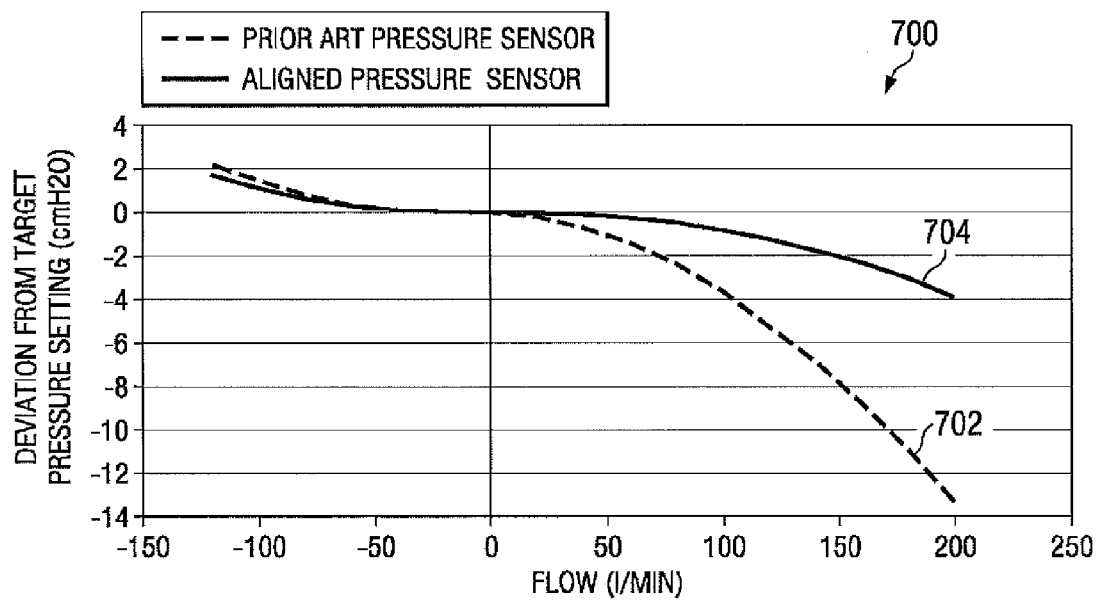
FIG. 7 illustrates a graph of deviation from an air pressure setting vs. air flow through a patient connection system for (a) a prior art pressure sensor and (b) an example pressure sensor according to the present disclosure.

FIG. 7 illustrates a graph 700 of the deviation of the actual delivered pressure from the target pressure setting versus the flow rate of gas delivered to patient 105, according to certain embodiments. As with FIG. 6, the horizontal axis indicates flow rate, in liters per minute. The vertical axis indicates the deviation from the target pressure setting for gas delivered to patient 105, in cmH$_2$O.

A first plot 702 indicates the deviation of the actual delivered pressure from the target pressure setting for a system controlled based on pressure measurements from a pressure sensor configured according to the prior art, e.g., pressure sensor 200 shown in FIG. 1A second plot 704 indicates the deviation of the actual delivered pressure from the target pressure setting for a system controlled based on pressure measurements from a pressure sensor configured according to certain embodiments of the present disclosure, e.g., pressure sensor 150 shown in FIGS. 3-4.

Plot lines 702 and 704 generally correspond to plot lines 602 and 604 in FIG. 6, discussed above. For example, lines 702 and 704 indicate that the deviation of the delivered pressure from the target pressure setting in the system controlled based on the prior art pressure sensor is significantly greater than the deviation of the delivered pressure from the target pressure setting in a system controlled based on a pressure sensor 150 according to certain embodiments of the present disclosure. Further, the difference in the deviations increases as a function of the flow rate.

It will be appreciated that while the disclosure is particularly described in the context of measuring and/or compensating for pressure difference in a conduit of a breathing assistance system, the apparatuses, techniques, and methods disclosed herein may be similarly applied in other contexts, e.g., measuring and/or compensating for pressure differences in other medical devices. Additionally, it should be understood that various changes, substitutions and alterations can be made herein without departing from the spirit and scope of the following claims.

What is claimed is:

1. A breathing assistance system for providing breathing assistance to a patient, comprising:
    a ventilation system for supplying a gas flow;
    a conduit operatively coupled to the ventilation system;
    a pressure sensor configured to measure a pressure of the gas flow through the conduit, the pressure sensor including a structure configured to create a localized pressure drop in the gas flow proximate the pressure sensor structure, the localized pressure drop substantially equivalent to a pressure drop occurring in the gas flow through the conduit from the pressure sensor to the patient; and
    a controller operable to control the pressure of the gas flow through the conduit based at least in part on the sensed pressure of the gas flow.

2. A breathing system according to claim 1, wherein the pressure sensor structure extends at least partially into an interior of the conduit.

3. A breathing system according to claim 1, wherein: a gas flows through the conduit in a first direction from an upstream location to a downstream location during positive gas flow toward a patient; and the pressure sensor structure defines an inlet side facing the downstream location, and a gas inlet formed in the inlet side, the gas inlet configured to receive gas for pressure measurement.

4. A breathing system according to claim 1, wherein: a gas flows through the conduit in a first direction from an upstream location to a downstream location during positive gas flow toward a patient; and the pressure sensor structure defines a leading side facing the upstream location, the leading side configured to produce a localized pressure drop in the gas flow as the gas flows around the leading side.

5. A breathing system according to claim 1, wherein: a gas flows through the conduit in a first direction from an upstream location to a downstream location during positive gas flow toward a patient; and the pressure sensor structure defines a gas inlet aligned generally parallel with the first direction of the gas flow.

6. A breathing system according to claim 1, wherein a portion of the pressure sensor structure extending into the conduit includes a substantially triangular or substantially T-shaped cross section.

7. A breathing system according to claim 1, wherein: a gas flows through the conduit in a first direction from an upstream location to a downstream location during positive gas flow toward a patient; and the pressure sensor structure defines: a leading side facing the upstream location and configured to affect the gas flow as the gas flow encounters the pressure sensor structure; and an inlet side facing the downstream location, the inlet side having a substantially flat structure and having a gas inlet formed therein for receiving gas to be measured.

8. A pressure sensor for use in a breathing assistance system for providing breathing assistance to a patient, comprising:
    a pressure sensor structure extending at least partially into an interior of a conduit operatively coupled to a ventilation system configured to supply a gas flow to a patient;
    wherein the pressure sensor structure is configured to affect the gas flow in the conduit to create a localized pressure drop proximate to the pressure sensor structure, the localized pressure drop substantially equivalent to a pressure drop occurring as a gas flows along the conduit from the pressure sensor structure to the patient; and
    a gas inlet formed in the pressure sensor structure, the gas inlet configured to receive the gas for pressure measurement.

9. A pressure sensor according to claim 8, wherein the gas inlet is formed in an inlet side of the pressure sensor structure configured to face a downstream end of the conduit during positive flow toward the patient.

10. A pressure sensor according to claim 8, wherein the pressure sensor structure defines a leading side configured to face an upstream end of the conduit during positive flow toward the patient, the leading side configured to substantially produce the localized pressure drop in the gas flow as gas flows around the leading side.

11. A pressure sensor according to claim 8, wherein the gas inlet is aligned generally parallel with a direction of the gas flow through the conduit from an upstream location to a downstream location.

12. A pressure sensor according to claim 8, wherein a portion of the pressure sensor structure extending into the conduit includes a substantially triangular or substantially T-shaped cross section.

13. A pressure sensor according to claim 8, wherein the pressure sensor structure defines: a leading side facing an upstream end of the conduit and configured to affect the gas flow as the gas flow encounters the pressure sensor structure; and an inlet side facing a downstream end of the conduit, the inlet side having a substantially flat structure having the gas inlet formed therein.

14. A method for controlling pressure delivered to a patient of a breathing assistance system, comprising:
    determining a target pressure setting;
    controlling a gas delivery device to generate a gas flow to a patient, the gas flow based at least on the target pressure setting;
    receiving pressure measurements from a pressure sensor operatively coupled to a conduit coupled to the gas delivery device, the pressure sensor including a structure configured to create a localized pressure drop in the gas flow proximate the pressure sensor structure, the localized pressure drop substantially equivalent to a pressure drop occurring as the gas flows along the conduit from the pressure sensor structure to the patient; and
    adjusting the gas delivery device based at least on the pressure measurements received from the pressure sensor.

15. A method according to claim 14, further comprising:
    comparing one or more pressure measurements received from the pressure sensor to the target pressure setting; and
    adjusting the gas delivery device based at least on the comparison between the one or more pressure measurements received from the pressure sensor and the target pressure setting.

16. A method according to claim 14, wherein:
    the gas flow generated by the gas delivery device flows through the conduit in a first direction from an upstream location to a downstream location during positive gas flow toward the patient; and
    the pressure sensor structure defines a gas inlet formed in an inlet side facing the downstream location, the gas inlet configured to receive a gas for pressure measurement.

17. A method according to claim 16, wherein the gas inlet is aligned generally parallel with the first direction of gas flow through the conduit from the upstream location to the downstream location.

* * * * *